(12) United States Patent
Gao et al.

(10) Patent No.: US 11,110,139 B2
(45) Date of Patent: Sep. 7, 2021

(54) APPLICATION OF ANTHOCYANIN EXTRACT IN PREPARING PHARMACEUTICAL COMPOSITION FOR PREVENTING AND TREATING CARDIAC TOXICITY INDUCED BY ANTHRACYCLINES AND PHARMACEUTICAL COMPOSITION

(71) Applicant: Northwest Institute of Plateau Biology, Chinese Academy of Sciences, Qinghai (CN)

(72) Inventors: Tingting Gao, Qinghai (CN); Hongtao Bi, Qinghai (CN); Lixin Wei, Qinghai (CN); Yuzhi Du, Qinghai (CN); Hongxia Yang, Qinghai (CN); Cen Li, Qinghai (CN)

(73) Assignee: Northwest Institute of Plateau Biology, Chinese Academy of Sciences, Qinghai (CN)

(*) Notice: Subject to any disclaimer, the term of this patent is extended or adjusted under 35 U.S.C. 154(b) by 569 days.

(21) Appl. No.: 15/831,411

(22) Filed: Dec. 5, 2017

(65) Prior Publication Data
US 2019/0000900 A1 Jan. 3, 2019

(30) Foreign Application Priority Data
Jun. 30, 2017 (CN) .......................... 201710532491.8

(51) Int. Cl.
*A61K 36/185* (2006.01)
*A61P 9/00* (2006.01)

(52) U.S. Cl.
CPC .............. *A61K 36/185* (2013.01); *A61P 9/00* (2018.01); *A61K 2236/333* (2013.01)

(58) Field of Classification Search
None
See application file for complete search history.

(56) References Cited

PUBLICATIONS

Zhang, et al., Food Funct., 8:2771. (Year: 2017).*
Wu, et al., Industrial Crops and Products, 66:229. (Year: 2015).*
Diamanti, et al., J. Agric. Food Chem., 62:3935. (Year: 2014).*
Choi, et al., Biofactors, 36:319. (Year: 2010).*
Huang, et al., Int. J. Mol. Sci., 17:1588. (Year: 2016).*
Sang, et al., Food Chemistry, 218:386. (Year: 2017).*
Zhe, et al., Protein & Peptide Letters, 23:424. (Year: 2016).*
Zheng, et al., Food Research International, 44:2041. (Year: 2011).*
Ma, et al., Food Chemistry, 194:296. (Year: 2016).*

* cited by examiner

*Primary Examiner* — Michael Barker
(74) *Attorney, Agent, or Firm* — Gang Yu (57) ABSTRACT

The disclosure provides an application of an anthocyanin extract in preparing a pharmaceutical composition for preventing and treating cardiac toxicity induced by Anthracyclines and the pharmaceutical composition, wherein the pharmaceutical composition comprises an effective dose of the anthocyanin extract; and the anthocyanin extract refers to an extract obtained from mature fruits of a zygophyllaceous *nitraria* plant and having a total anthocyanin content greater than 700 mg CGE/g and a total antioxidant capacity greater than 200 mg TE/g. Cytobiology and molecular biology studies prove that the anthocyanin extract has obvious protection effect to cardiomyocyte toxicity damage induced by anthracyclines and may be used for preventing and alleviating cardiotoxicity of an antharcyclines anticancer drug, thereby expanding a clinical application of the antharcyclines anticancer drug and relieving toxic and side effects brought by the antharcyclines anticancer drug to a patient and pain of a chemotherapy patient. And additionally, the raw material sources for the anthocyanin extract are wide, the cost is low and the use is safe.

5 Claims, 11 Drawing Sheets

APPLICATION OF ANTHOCYANIN EXTRACT IN PREPARING PHARMACEUTICAL COMPOSITION FOR PREVENTING AND TREATING CARDIAC TOXICITY INDUCED BY ANTHRACYCLINES AND PHARMACEUTICAL COMPOSITION

TECHNICAL FIELD

The present disclosure relates to the technical field of biomedicines, and more particularly, to an application of an anthocyanin extract in preparing a pharmaceutical composition for preventing and treating cardiac toxicity induced by Anthracyclines and the pharmaceutical composition.

BACKGROUND

Anthracyclines are a kind of chemotherapeutic drug derived from *Streptomyces peucetius* var. *caesius*. In chemical structures of anthracyclines antibiotics, there have an anthracene, a six-membered ring as a basic band side chain, and an amino sugar compound. Brockmann et al. found a first anthracyclines antibiotic (rhodomycin) in an *S. purpurascen* culture solution in early 1950. Since then, more and more anthracyclines antibiotics are found one after another. The anthracyclines antibiotics have remarkable characteristics such as the anticancer spectrum is wide, the action is powerful, the efficacy of treatment of multiple malignant solid tumors and hematological malignant tumors like leukemia, breast cancer, lung cancer, stomach cancer and lymphoma is very good, and it is also effective to a hypoxic cell. With the definite therapeutic effect, the anthracyclines antibiotics are indispensable and the combined therapy on the basis of the anthracyclines is served as a standard scheme for first-line treatment. At present, the anthracyclines anticancer drugs frequently used in clinic include doxorubicin (DOX), daunorubicin (DNR), epirubicin, pirarubicin, aclacinomycin B, idarubicin, valrubicin, mitoxantrone and the like, among which the doxorubicin is one of the most common anticancer drugs. However, the anthracyclines are dose-dependent and accumulative cardiotoxic and almost 10% of patients who received DOX treatment have cardiac complications after nearly 10 years of chemotherapy. As a result, its clinical applications are limited and its cardiotoxicity even may be life-threatening.

The anthracyclines are applied clinically for many years, but so far, there still haven't a complete explanation on its mechanisms to cause the cardiotoxicity. Currently, it is widely believed that increased oxidative stress, calcium overload, energy metabolic disorder, mitochondria damage, cell apoptosis and the like caused by reactive oxygen species (ROS) and lipid peroxidation play an important role in producing the DOX cardiotoxicity. Up to now, the main mechanisms or hypotheses include oxidative stress, iron mechanism, calcium disorder, mitochondria damage and cell apoptosis, etc. To solve the limitations of the anthracyclines in clinical applications, investigators implement a lot of studies on auxiliary therapeutic drugs for prevention and treatment of the cardiotoxicity caused by the anthracyclines, and these auxiliary therapeutic drugs mainly include a radical scavenger, an antioxidant, a ferric ion chelator, a calcium antagonist, a mitochondrial protectant, an apoptotic inhibitor and so on.

Along with the social development, there is an increased interest in concerning negative effects brought by a chemical drug to health and living environments of human beings. To return to nature and to protect environment have become a trend to deal with relations between the human beings and the environment. Because a natural drug is from nature and has small toxic and side effects, it is highly appraised with unique advantages in treatment of difficult miscellaneous diseases. In recent years, the natural anthracyclines cardiotoxicity protecting drugs that have been found include a 20(S)-ginsenoside RH2 (ZL200610069844.7), a radix glycyrrhizae extract (ZL200810099467.0), a biological flavone compound (ZL201010201577.0), a 23-hydroxybetulinic acid (ZL201010514113.5), a neonuezhenide (ZL201410134883.5), a berberine derivative (ZL201410361037.7) and a traditional Chinese medicinal combined extract (ZL200810041276.9), etc.

An anthocyanin is a kind of flavonoid compound formed by combining an anthocyanidin with sugar via a glycoside bond and widely exists in a cell sap of flower, fruit, stem, leaf and root organs of a plant. Because of its special function, the anthocyanin is applied to scavenging in-vivo radicals, proliferating xanthin, resisting a tumor, a cancer and an inflammation, inhibiting lipid peroxidation and platelet aggregation, preventing diabetes, losing weight, protecting an eyesight and the like. As a natural pigment, the anthocyanin is safe and nontoxic, has many healthcare functions to a human body and has been widely applied to industries such as foods, healthcare products, cosmetics and medicines. However, there hasn't a report on a natural compound anthocyanins auxiliary drug for the cardiotoxicity of the anthracycline antibiotics till date.

SUMMARY

The present disclosure is intended to provide an application of an anthocyanin extract in preparing a pharmaceutical composition for preventing and treating cardiac toxicity induced by Anthracyclines and the pharmaceutical composition, so as to provide a safe and nontoxic auxiliary therapeutic drug for anthracyclines.

To this end, according to one aspect of the present disclosure, a pharmaceutical composition for preventing and treating cardiac toxicity induced by Anthracyclines is provided. The pharmaceutical composition includes an effective dose of an anthocyanin extract; and the anthocyanin extract refers to an extract obtained from mature fruits of a zygophyllaceous *nitraria* plant and having a total anthocyanin content greater than 700 mg CGE/g and a total antioxidant capacity greater than 200 mg TE/g.

Further, an anthocyanidin as a source of the anthocyanin extract includes cyanidin, delphinidin, malvidin, pelargonidin, peonidin and petunidin.

Further, the anthocyanin extract includes six or more selected from groups composed of cyanidin-3-O-diglucoside, cyanidin-3-O-sambubioside, cyanidin-3-O-(cis-6"-O-coumaroyl)-diglucoside, cyanidin-3-O-(trans-6"-O-coumaroyl)-diglucoside, cyanidin-3-O-(6"-O-coumaroyl)-glucoside, delphinidin-3-O-(6"-O-coumaroyl)-glucoside, 5-O-glucoside, delphinidin-3-O-(6"-O-coumaroyl)-glucoside, malvidin-3-O-glucoside, malvidin-3-O-(6"-O-acetyl)-glucoside, malvidin-3-O-(6"-O-coumaroyl)-glucoside, 5-O-glucoside, malvidin-3-O-(cis-6"-O-coumaroyl)-glucoside, malvidin-3-O-(trans-6"-O-coumaroyl)-glucoside, pelargonidin-3-O-(6"-O-coumaroyl)-diglucoside, peonidin-3-O-(6"-O-coumaroyl)-glucoside, peonidin-3-O-(6"-O-coumaroyl)-glucoside, 5-O-glucoside and petunidin-3-O-(6"-O-coumaroyl)-glucoside; and the anthocyanidin as the source of the anthocyanin extract includes the cyanidin, the delphinidin, the malvidin, the pelargonidin, the peonidin and the petunidin.

Further, the anthocyanin extract is prepared by the following method: adding 60-90% ethanol to pomaces, which are produced by *nitraria* fruits or after the *nitraria* fruits are squeezed into juice, according to a solid-liquid ratio of 1:15-1:30 g/mL and extracting for 30-90 min at 55-65° C.; concentrating an extracting solution under a reduced pressure till there is no ethanol, separating by a weakly polar macroporous adsorption resin, rinsing with three times of water by a column volume, then rinsing with the 60-90% ethanol, collecting an effluent, concentrating and drying to obtain the anthocyanin extract.

Further, the anthracyclines are one or more of DOX, DNR, aclacinomycin, epirubicin, pirarubicin, idarubicin, valrubicin or mitoxantrone.

Further, a dosage form of the pharmaceutical composition is any one of a capsule, a tablet, an oral liquid, a granule and a dropping pill.

According to another aspect of the present disclosure, an application of an anthocyanin extract in preparing a pharmaceutical composition for preventing and treating cardiac toxicity induced by Anthracyclines is provided, wherein the anthocyanin extract refers to an extract obtained from mature fruits of a zygophyllaceous *nitraria* plant and having a total anthocyanin content greater than 700 mg CGE/g and a total antioxidant capacity greater than 200 mg TE/g.

Further, an anthocyanidin as a source of the anthocyanin extract includes cyanidin, delphinidin, malvidin, pelargonidin, peonidin and petunidin.

Further, the anthocyanin extract includes six or more selected from groups composed of cyanidin-3-O-diglucoside, cyanidin-3-O-sambubioside, cyanidin-3-O-(cis-6"-O-coumaroyl)-diglucoside, cyanidin-3-O-(trans-6"-O-coumaroyl)-diglucoside, cyanidin-3-O-(6"-O-coumaroyl)-glucoside, delphinidin-3-O-(6"-O-coumaroyl)-glucoside, 5-O-glucoside, delphinidin-3-O-(6"-O-coumaroyl)-glucoside, malvidin-3-O-glucoside, malvidin-3-O-(6"-O-acetyl)-glucoside, malvidin-3-O-(6"-O-coumaroyl)-glucoside, 5-O-glucoside, malvidin-3-O-(cis-6"-O-coumaroyl)-glucoside, malvidin-3-O-(trans-6"-O-coumaroyl)-glucoside, pelargonidin-3-O-(6"-O-coumaroyl)-diglucoside, peonidin-3-O-(6"-O-coumaroyl)-glucoside, peonidin-3-O-(6"-O-coumaroyl)-glucoside, 5-O-glucoside and petunidin-3-O-(6"-O-coumaroyl)-glucoside; and the anthocyanidin as the source of the anthocyanin extract includes the cyanidin, the delphinidin, the malvidin, the pelargonidin, the peonidin and the petunidin.

Further, the anthocyanin extract is prepared by the following method: adding 60-90% ethanol to pomaces, which are produced by *nitraria* fruits or after the *nitraria* fruits are squeezed into juice, according to a solid-liquid ratio of 1:15-1:30 g/mL and extracting for 30-90 min at 55-65° C.; concentrating an extracting solution under a reduced pressure till there is no ethanol, separating by a weakly polar macroporous adsorption resin, rinsing with three times of water by a column volume, then rinsing with the 60-90% ethanol, collecting an effluent, concentrating and drying to obtain the anthocyanin extract.

Cytobiology and molecular biology studies prove that the anthocyanin extract has obvious protection effect to anthracyclines cardiomyocyte toxicity damage and may be used for preventing and alleviating cardiotoxicity of an antharcyclines anticancer drug, thereby expanding a clinical application of the antharcyclines anticancer drug and relieving toxic and side effects brought by the antharcyclines anticancer drug to a patient and pain to a chemotherapy patient. And additionally, the raw material sources for the anthocyanin extract are wide, the cost is low and the use is safe.

BRIEF DESCRIPTION OF THE DRAWINGS

The accompanying drawings are described here to provide further understanding of the present disclosure, and form a part of the present disclosure. The schematic embodiments and description of the present disclosure are adopted to explain the present disclosure, and do not form improper limits to the present disclosure. In the drawings;

FIG. 2-1 shows a mass spectrogram of each chromatographic peak in a *nitraria* anthocyanin extract according to an embodiment of the present disclosure;

FIG. 2-2 shows a mass spectrogram (continued) of each chromatographic peak in a *nitraria* anthocyanin extract according to an embodiment of the present disclosure;

FIG. 7A shows a key gene protein expression and Caspase cascade reaction in cell apoptosis of a cardiomyocyte H9c2 in embodiment 5, FIG. 7A is a western-blot result.

DETAILED DESCRIPTION OF THE EMBODIMENTS

It is to be noted that the examples of the present application and the characteristics of the examples may be combined with each other if there is no conflict. The present disclosure will be described below with reference to the drawings and examples in detail.

Inventors of the present disclosure discover that the anthocyanin extract may be used for preventing and treating the cardiac toxicity induced by Anthracyclines. Therefore, the development of natural drugs based the anthocyanins existing in nature massively, not only may a safe and nontoxic auxiliary therapeutic drug be provided for the anthracyclines, but also the rapidly increased treatment expenses of the patient due to a high-cost auxiliary drug such as dexrazoxane (ICRF-187) may be avoided. And the anthocyanin extract is of a practical guiding significance to the development of a novel anthracyclines cardiac protective agent.

According to a typical embodiment of the present disclosure, a pharmaceutical composition for preventing and treating cardiac toxicity induced by Anthracyclines is provided; the pharmaceutical composition includes an effective dose of an anthocyanin extract; and the anthocyanin extract refers to an extract obtained from mature fruits of a zygophyllaceous *nitraria* plant (such as *Nitraria tangutorum* Bobr., *Nitraria sibirica* Pall., *Nitraria roborowskii* Kom. and *Nitraria praevisa* Bobr.) and having a total anthocyanin content greater than 700 mg CGE/g and a total antioxidant capacity greater than 200 mg TE/g.

Preferably, an anthocyanidin as a source of the anthocyanin extract includes cyanidin, delphinidin, malvidin, pelargonidin, peonidin and petunidin.

Preferably, the anthocyanin extract includes six or more selected from groups composed of cyanidin-3-O-diglucoside, cyanidin-3-O-sambubioside, cyanidin-3-O-(cis-6"-O-coumaroyl)-diglucoside, cyanidin-3-O-(trans-6"-O-coumaroyl)-diglucoside, cyanidin-3-O-(6"-O-coumaroyl)-glucoside, delphinidin-3-O-(6"-O-coumaroyl)-glucoside, 5-O-glucoside, delphinidin-3-O-(6"-O-coumaroyl)-glucoside, malvidin-3-O-glucoside, malvidin-3-O-(6"-O-acetyl)-glucoside, malvidin-3-O-(6"-O-coumaroyl)-glucoside, 5-O-glucoside, malvidin-3-O-(cis-6"-O-coumaroyl)-glucoside, malvidin-3-O-(trans-6"-O-coumaroyl)-glucoside, pelargonidin-3-O-(6"-O-coumaroyl)-diglucoside, peonidin-3-O-(6"-O-coumaroyl)-glucoside, peonidin-3-O-(6"-O-coumaroyl)-glucoside, 5-O-glucoside and petunidin-3-O-(6"-O-coumaroyl)-glucoside; and the anthocyanidin as the source of the anthocyanin extract includes the cyanidin, the delphinidin, the malvidin, the pelargonidin, the peonidin and the petunidin.

Figure 1:
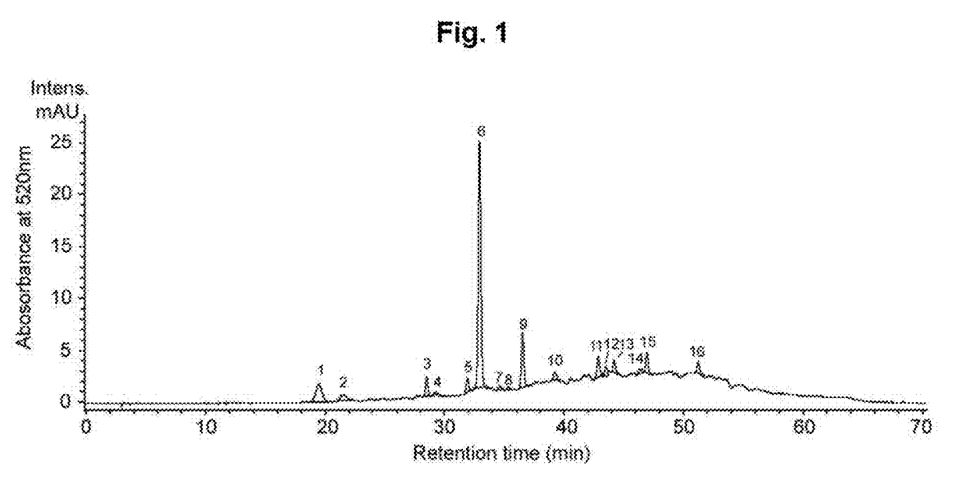
FIG. 1 shows a high performance liquid chromatography (HPLC) chromatogram of a *nitraria* anthocyanin extract according to an embodiment of the present disclosure.
Figure 21:
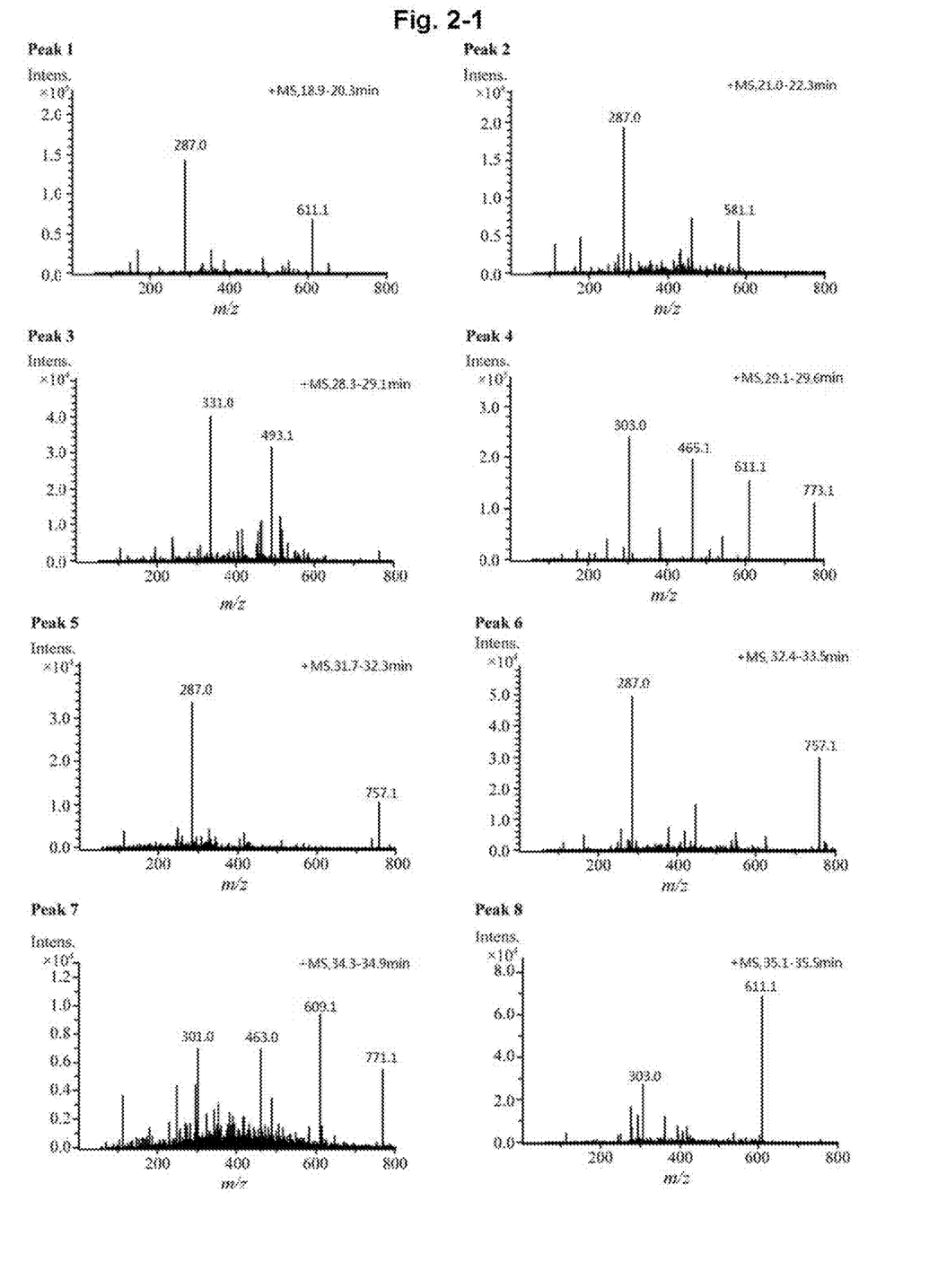
Figure 22:
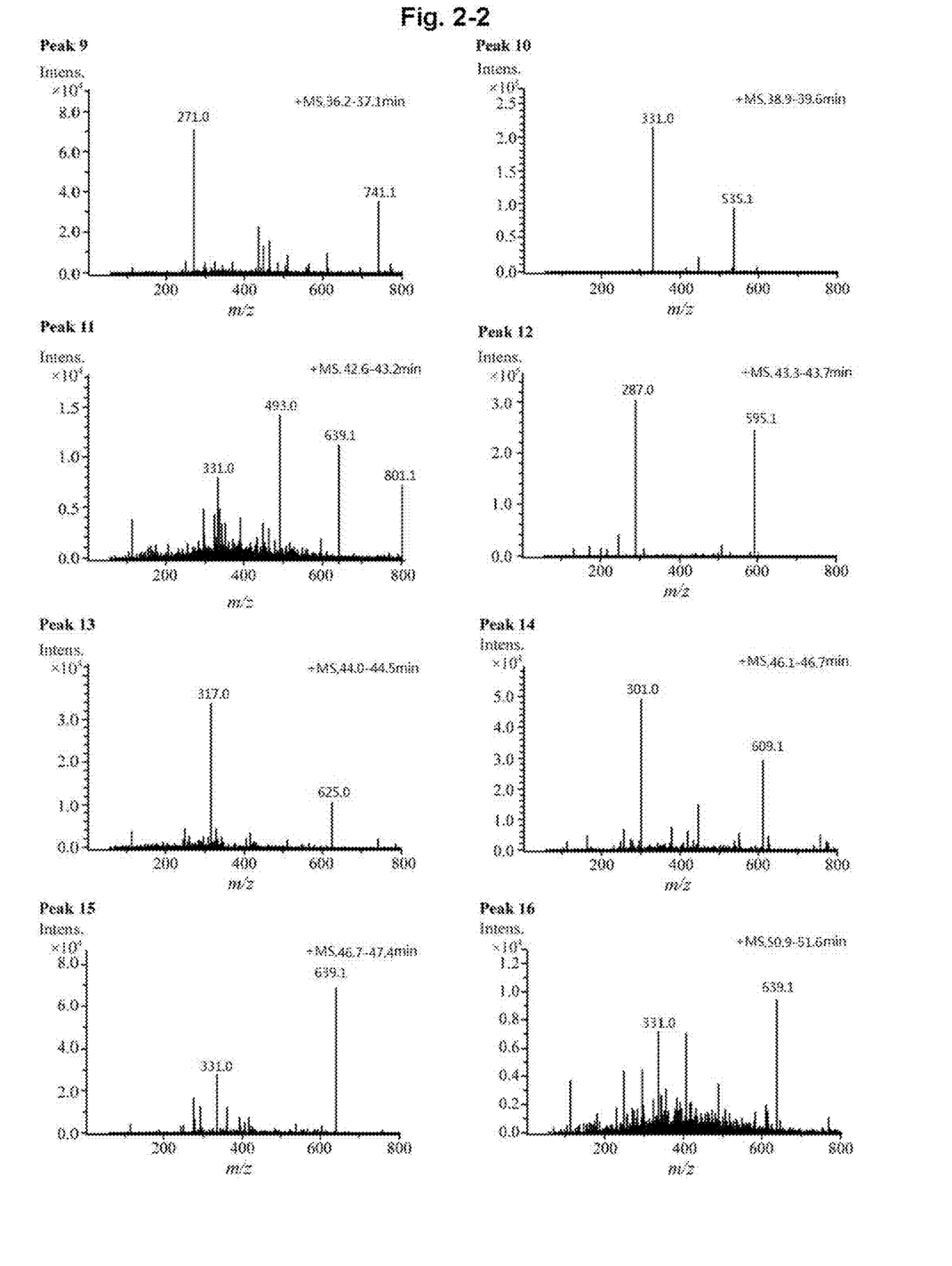

Preferably, the anthocyanin extract is prepared by the following method: adding 60-90% ethanol (preferably 70% ethanol) to pomaces, which are produced by *nitraria* fruits or after the *nitraria* fruits are squeezed into juice, according to a solid-liquid ratio of 1:15-1:30 g/mL and extracting for 30-90 min at 55-65° C.; concentrating an extracting solution under a reduced pressure till there is no ethanol, separating by a weakly polar macroporous adsorption resin, rinsing with three times of water by a column volume, then rinsing with the 60-90% ethanol, collecting an effluent, concentrating and drying to obtain the anthocyanin extract. Compositions of the anthocyanins in the extract are as shown in table 1, FIG. 1, FIG. 2-1 and FIG. 2-2, wherein the table 1 shows a composition table of sixteen anthocyanins in the *nitraria* anthocyanin extract, FIG. 1 shows an HPLC chromatogram of the *nitraria* anthocyanin extract, and FIG. 2-1 and FIG. 2-2 show a mass spectrogram of each chromatographic peak in the *nitraria* anthocyanin extract.

TABLE 1

Composition Table of Sixteen Anthocyanins in the Nitraria Anthocyanin Extract

| Serial No. | Name of Anthocyanins | Retention Time (min) | [M]+ (m/z) | Fragment Ions |
|---|---|---|---|---|
| 1 | Cyanidin-3-O-diglucoside | 19.5 | 611 | 287 |
| 2 | Cyanidin-3-O-sambubioside | 21.5 | 581 | 287 |
| 3 | Malvidin-3-O-glucoside | 28.5 | 493 | 331 |
| 4 | Delphinidin-3-O-(6"-O-coumaroyl)-glucoside, 5-O-glucoside | 29.2 | 773 | 611/465/303 |
| 5 | Cyaniden-3-O-(cis-6"-O-coumaroyl)-diglucoside | 31.9 | 757 | 287 |
| 6 | Cyanidin-3-O-(trans-6"-O-coumaroyl)-diglucoside | 32.9 | 757 | 287 |
| 7 | Peonidin-3-O-(6"-O-coumaroyl)-glucoside, 5-O-glucoside | 34.6 | 771 | 609/463/301 |
| 8 | Dephinidin-3-O-(6"-O-coumaroyl)-glucoside | 35.3 | 611 | 303 |
| 9 | Pelargonidin-3-O-(6"-O-coumaroyl)-diglucosid | 36.5 | 741 | 271 |
| 10 | Malvidin-3-O-(6"-O-acetyl)-glucoside | 39.2 | 535 | 331 |
| 11 | Malvidin-3-O-(6"-O-coumaroyl)-gludoside, 5-O-glucoside | 42.9 | 801 | 639/493/331 |
| 12 | Cyanidin-3-O-(6"-O-coumaroyl)-glucoside | 43.5 | 595 | 287 |
| 13 | Petunidin-3-O-(6"-O-cournaroyl)-glucoside | 44.2 | 625 | 317 |
| 14 | Peonidin-3-O-(6"-O-coumaroyl)-glucoside | 46.3 | 609 | 301 |

TABLE 1-continued

Composition Table of Sixteen Anthocyanins in the Nitraria Anthocyanin Extract

| Serial No. | Name of Anthocyanins | Retention Time (min) | [M]+ (m/z) | Fragment Ions |
|---|---|---|---|---|
| 15 | Malvidin-3-O-(cis-6"-O-coumaroyl)-glucoside | 46.9 | 639 | 331 |
| 16 | Malvidin-3-O-(trans-6"-O-coumaroyl)-glucoside | 51.2 | 639 | 331 |

According to a typical embodiment of the present disclosure, the anthracyclines are one or more of DOX, DNR, aclacinomycin, epirubicin, pirarubicin, idarubicin, valrubicin or mitoxantrone.

According to a typical embodiment of the present disclosure, a dosage form of the pharmaceutical composition is any one of a capsule, a tablet, an oral liquid, a granule and a dropping pill.

According to a typical embodiment of the present disclosure, an application of an anthocyanin extract in preparing a pharmaceutical composition for preventing and treating cardiac toxicity induced by Anthracyclines is provided, wherein the anthocyanin extract refers to an extract obtained from mature fruits of a zygophyllaceous *nitraria* plant and having a total anthocyanin content greater than 700 mg CGE/g and a total antioxidant capacity greater than 200 mg TE/g.

Preferably, an anthocyanidin as a source of the anthocyanin extract includes cyanidin, delphinidin, malvidin, pelargonidin, peonidin and petunidin.

Preferably, the anthocyanin extract includes six or more selected from groups composed of cyanidin-3-O-diglucoside, cyanidin-3-O-sambubioside, cyanidin-3-O-(cis-6"-O-coumaroyl)-diglucoside, cyanidin-3-O-(trans-6"-O-coumaroyl)-diglucoside, cyanidin-3-O-(6"-O-coumaroyl)-glucoside, delphinidin-3-O-(6"-O-coumaroyl)-glucoside, 5-O-glucoside, delphinidin-3-O-(6"-O-coumaroyl)-glucoside, malvidin-3-O-glucoside, malvidin-3-O-(6"-O-acetyl)-glucoside, malvidin-3-O-(6"-O-coumaroyl)-glucoside, 5-O-glucoside, malvidin-3-O-(cis-6"-O-coumaroyl)-glucoside, malvidin-3-O-(trans-6"-O-coumaroyl)-glucoside, pelargonidin-3-O-(6"-O-coumaroyl)-diglucoside, peonidin-3-O-(6"-O-coumaroyl)-glucoside, peonidin-3-O-(6"-O-coumaroyl)-glucoside, 5-O-glucoside and petunidin-3-O-(6"-O-coumaroyl)-glucoside; and the anthocyanidin as the source of the anthocyanin extract includes the cyanidin, the delphinidin, the malvidin, the pelargonidin, the peonidin and the petunidin.

Preferably, the anthocyanin extract is prepared by the following method: adding 60-90% ethanol to pomaces, which are produced by *nitraria* fruits or after the *nitraria* fruits are squeezed into juice, according to a solid-liquid ratio of 1:15-1:30 g/mL and extracting for 30-90 min at 55-65° C.; concentrating an extracting solution under a reduced pressure till there is no ethanol, separating by a weakly polar macroporous adsorption resin, rinsing with three times of water by a column volume, then rinsing with the 60-90% ethanol, collecting an effluent, concentrating and drying to obtain the anthocyanin extract.

According to a typical embodiment of the present disclosure, the anthracyclines are one or more of DOX, DNR, aclacinomycin, epirubicin, pirarubicin, idarubicin, valrubicin or mitoxantrone.

According to a typical embodiment of the present disclosure, a dosage form of the pharmaceutical composition is any one of a capsule, a tablet, an oral liquid, a granule and a dropping pill.

According to a typical embodiment of the present disclosure, an application of an anthocyanin extract in preventing and treating cardiac toxicity induced by Anthracyclines is provided, wherein the anthocyanin extract refers to an extract obtained from mature fruits of a zygophyllaceous *nitraria* plant and having a total anthocyanin content greater than 700 mg CGE/g and a total antioxidant capacity greater than 200 mg TE/g.

Preferably, an anthocyanidin as a source of the anthocyanin extract includes cyanidin, delphinidin, malvidin, pelargonidin, peonidin and petunidin.

Preferably, the anthocyanin extract includes six or more selected from groups composed of cyanidin-3-O-diglucoside, cyanidin-3-O-sambubioside, cyanidin-3-O-(cis-6"-O-coumaroyl)-diglucoside, cyanidin-3-O-(trans-6"-O-coumaroyl)-diglucoside, cyanidin-3-O-(6"-O-coumaroyl)-glucoside, delphinidin-3-O-(6"-O-coumaroyl)-glucoside, 5-O-glucoside, delphinidin-3-O-(6"-O-coumaroyl)-glucoside, malvidin-3-O-glucoside, malvidin-3-O-(6"-O-acetyl)-glucoside, malvidin-3-O-(6"-O-coumaroyl)-glucoside, 5-O-glucoside, malvidin-3-O-(cis-6"-O-coumaroyl)-glucoside, malvidin-3-O-(trans-6"-O-coumaroyl)-glucoside, pelargonidin-3-O-(6"-O-coumaroyl)-diglucoside, peonidin-3-O-(6"-O-coumaroyl)-glucoside, peonidin-3-O-(6"-O-coumaroyl)-glucoside, 5-O-glucoside and petunidin-3-O-(6"-O-coumaroyl)-glucoside; and the anthocyanidin as the source of the anthocyanin extract includes the cyanidin, the delphinidin, the malvidin, the pelargonidin, the peonidin and the petunidin.

Preferably, the anthocyanin extract is prepared by the following method: adding 60-90% ethanol to pomaces, which are produced by *nitraria* fruits or after the *nitraria* fruits are squeezed into juice, according to a solid-liquid ratio of 1:15-1:30 g/mL and extracting for 30-90 min at 55-65° C.; concentrating an extracting solution under a reduced pressure till there is no ethanol, separating by a weakly polar macroporous adsorption resin, rinsing with three times of water by a column volume, then rinsing with the 60-90% ethanol, collecting an effluent, concentrating and drying to obtain the anthocyanin extract.

According to a typical embodiment of the present disclosure, the anthracyclines are one or more of DOX, DNR, aclacinomycin, epirubicin, pirarubicin, idarubicin, valrubicin or mitoxantrone.

According to a typical embodiment of the present disclosure, a method for preventing and treating cardiac toxicity induced by Anthracyclines is provided, which includes that a pharmaceutical composition is used to implement protection on a heart. The pharmaceutical composition includes an effective dose of an anthocyanin extract, and the anthocyanin extract refers to an extract obtained from mature fruits of a zygophyllaceous *nitraria* plant (such as *nitraria tangutorum* bobr., *nitraria sibirica* pall., *nitraria roborowskii* kom. and *nitraria praevisa* bobr.) and having a total anthocyanin content greater than 700 mg CGE/g and a total antioxidant capacity greater than 200 mg TE/g.

The beneficial effects of the present disclosure will be further described below in conjunction with the examples.

Embodiment 1

Figure 3:
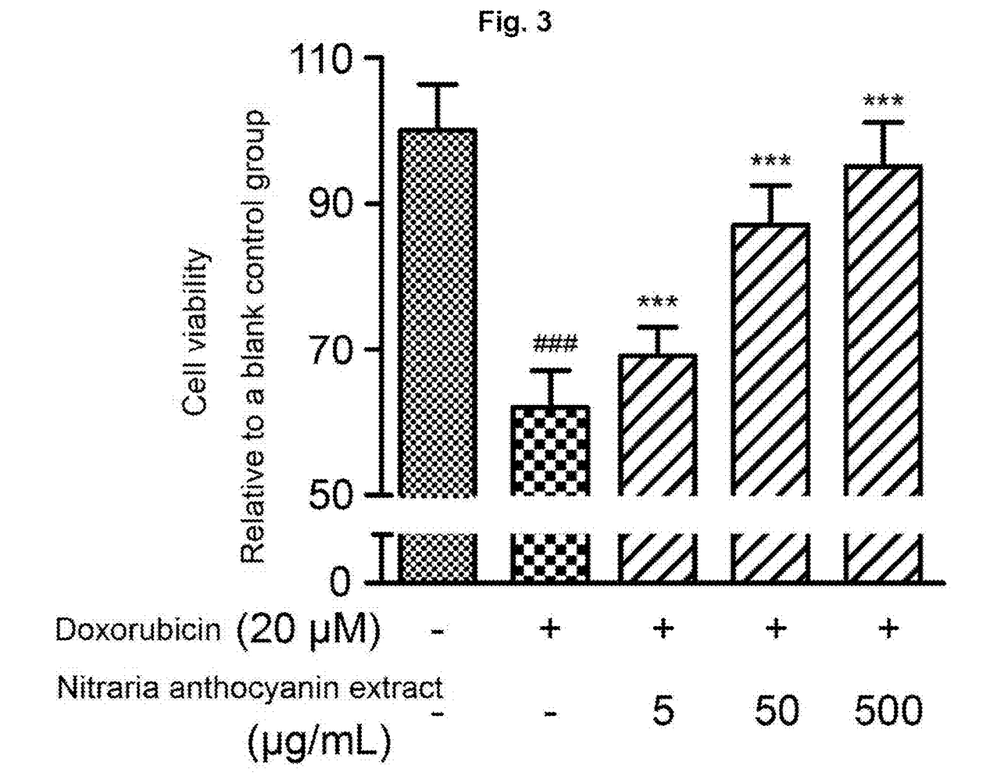
FIG. 3 shows a cell viability of a cardiomyocyte H9c2 in embodiment 1.

A rat cardiomyocyte cell line H9c2: a DMEM culture medium (containing 10% new-born calf serum, 2 mM glutamate and 1% streptomycin/penicillin) was employed to culture, and a culture condition was an aseptic environment at 37° C. and 5% $CO_2$. The culture medium was replaced once every 2-3 d, and when cells were cultured for 24 h and 80% were aggregated, was transferred to a 96-well plate with a cell density being $1 \times 10^5$/well; after the cells were continued to culture for 24 h, a medicament treatment was performed. A control group, a model group (containing 20 μM DOX), and a *nitraria* anthocyanin extract experimental group (containing 20 μM DOX and 5-500 μg/mL *nitraria* anthocyanin extract) were respectively provided, and after they were treated for 24 h, a cell viability was detected by an MTT method. According to experimental results as shown in FIG. 3, after the 20 μM DOX is treated for 24 h, the cell viability of the H9c2 is significantly reduced to 62.12% of a normal cell (P<0.001); as the *nitraria* anthocyanin extract can significantly inhibit cardiomyocyte viability damage caused by the DOX (P<0.001), after the DOX and the 5-500 μg/mL *nitraria* anthocyanin extract are co-treated for 24 h, the cell viability is 69.02%-95.61% of the normal cardiomyocyte. It is indicated that the *nitraria* anthocyanin extract has obvious protection effect to the cardiomyocyte viability damage caused by the DOX.

Embodiment 2

Figure 4:
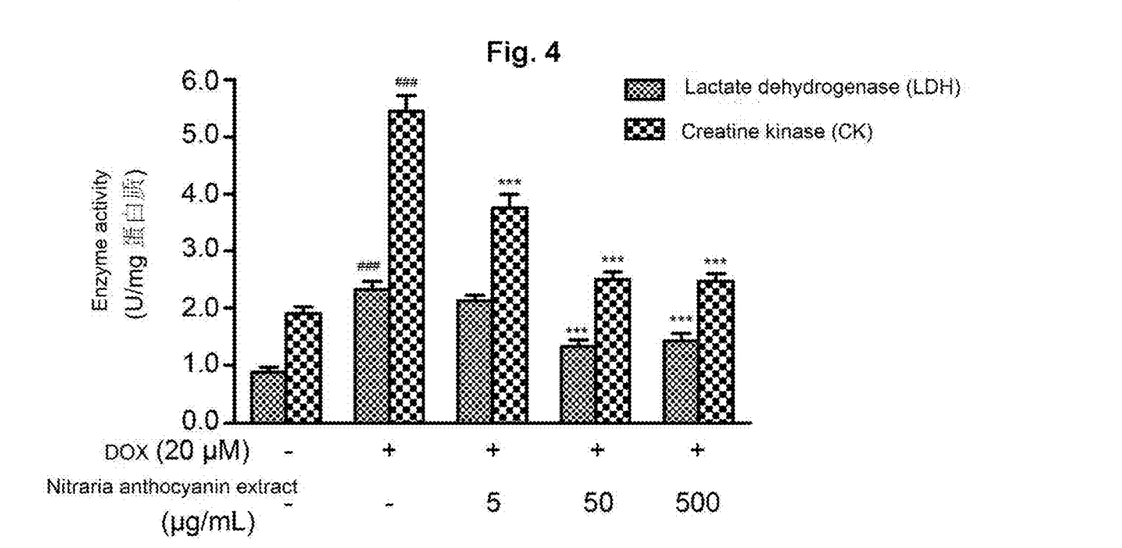
FIG. 4 shows a lactate dehydrogenase (LDH) and creatine kinase (CK) level of an extracellular fluid of a cardiomyocyte H9c2 in embodiment 2.

A rat cardiomyocyte cell line H9c2: a DMEM culture medium (containing 10% new-born calf serum, 2 mM glutamate and 1% streptomycin/penicillin) was employed to culture, and a culture condition was an aseptic environment at 37° C. and 5% $CO_2$. The culture medium was replaced once every 2-3 d, and when cells were cultured for 24 h and 80% were aggregated, a medicament treatment was performed. A control group, a model group (containing 20 μM DOX), and a *nitraria* anthocyanin extract experimental group (containing 20 μM DOX and 5-500 μg/mL *nitraria* anthocyanin extract) were respectively provided, after they were treated for 24 h, an extracellular fluid was collected, and LDH and CK levels in the extracellular fluid were detected by employing LDH and CK array kits. According to experimental results as shown in FIG. 4, after the 20 μM DOX is treated for 24 h, the LDH and CK levels in the extracellular fluid of the H9c2 are respectively increased to 2.65 times and 2.87 times of a normal cell (P<0.001); as the *nitraria* anthocyanin extract can significantly inhibit an increase of the LDH and CK levels in the cardiomyocyte extracellular fluid caused by the DOX (P<0.001), after the DOX and the 5-500 μg/mL *nitraria* anthocyanin extract are co-treated for 24 h, the LDH and CK levels in the cardiomyocyte extracellular fluid respectively are 1.51-2.42 times and 1.30-1.98 times of the normal cell. It is indicated that the *nitraria* anthocyanin extract has obvious protection effect to cardiomyocyte membrane structural damage caused by the DOX.

Embodiment 3

Figure 5:
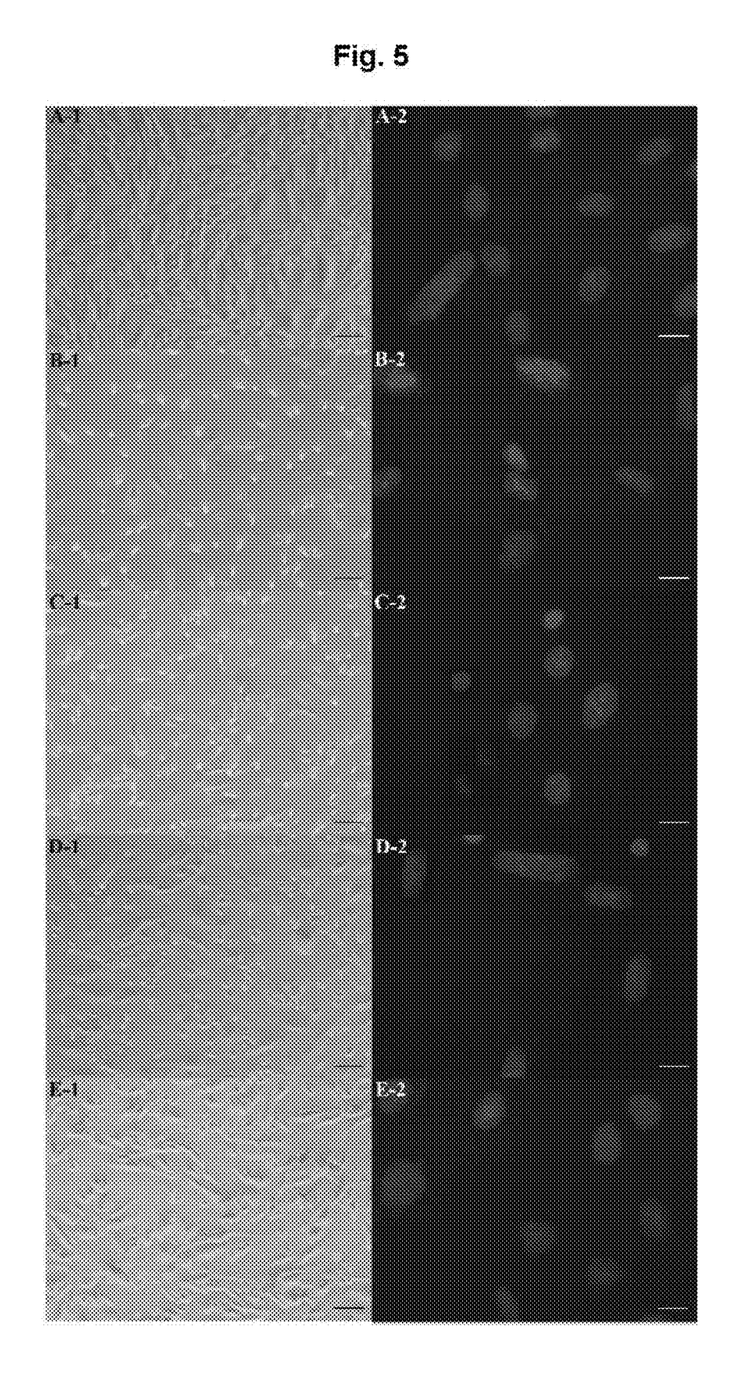
FIG. 5 shows a cell and cell nucleus morphological diagram of a cardiomyocyte H9c2 in embodiment 3, wherein A1-E1 are a cell morphological diagram of the cardiomyocyte H9c2 observed by an inverted phase contrast microscope, A2-E2 are a result map observed by a fluorescence microscope after fluorescence staining of the cell nucleus of the cardiomyocyte H9c2, a measuring scale is 25 μm, A-1 and A-2 are blank control groups, B1 and B2 are DOX treated cell damage model groups, C1 and C2 are *nitraria* anthocyanin extract treated low-dose groups (5 μg/mL), D1 and D2 are *nitraria* anthocyanin extract treated dose groups (50 μg/mL), and E1 and E2 are *nitraria* anthocyanin extract treated high-dose groups (500 μg/mL)

A rat cardiomyocyte cell line H9c2: a DMEM culture medium (containing 10% new-born calf serum, 2 mM glutamate and 1% streptomycin/penicillin) was employed to culture, and a culture condition was an aseptic environment at 37° C. and 5% $CO_2$. The culture medium was replaced once every 2-3 d, and when cells were cultured for 24 h and 80% were aggregated, a medicament treatment was performed. A control group, a model group (containing 20 μM DOX), and a *nitraria* anthocyanin extract experimental group (containing 20 μM DOX and 5-500 μg/mL *nitraria* anthocyanin extract) were respectively provided, and after they were treated for 24 h, a phase contrast microscope was employed to observe a morphological change of a cell. And subsequently, after a cell nucleus was dyed for 30 min with a Hoechst 33258 dye, an inverted fluorescence microscope was employed to observe a structural change of the cell nucleus. According to experimental results as shown in FIG. 5, the 5-500 μg/mL *nitraria* anthocyanin extract can obviously protect cell contraction, cell membrane foaming, heteroplasmon enhancement and chromatin condensation from an edge caused by the DOX. It is indicated that the *nitraria* anthocyanin extract has obvious protection effect to cardiomyocyte structural damage caused by the DOX.

Embodiment 4

Figure 6:
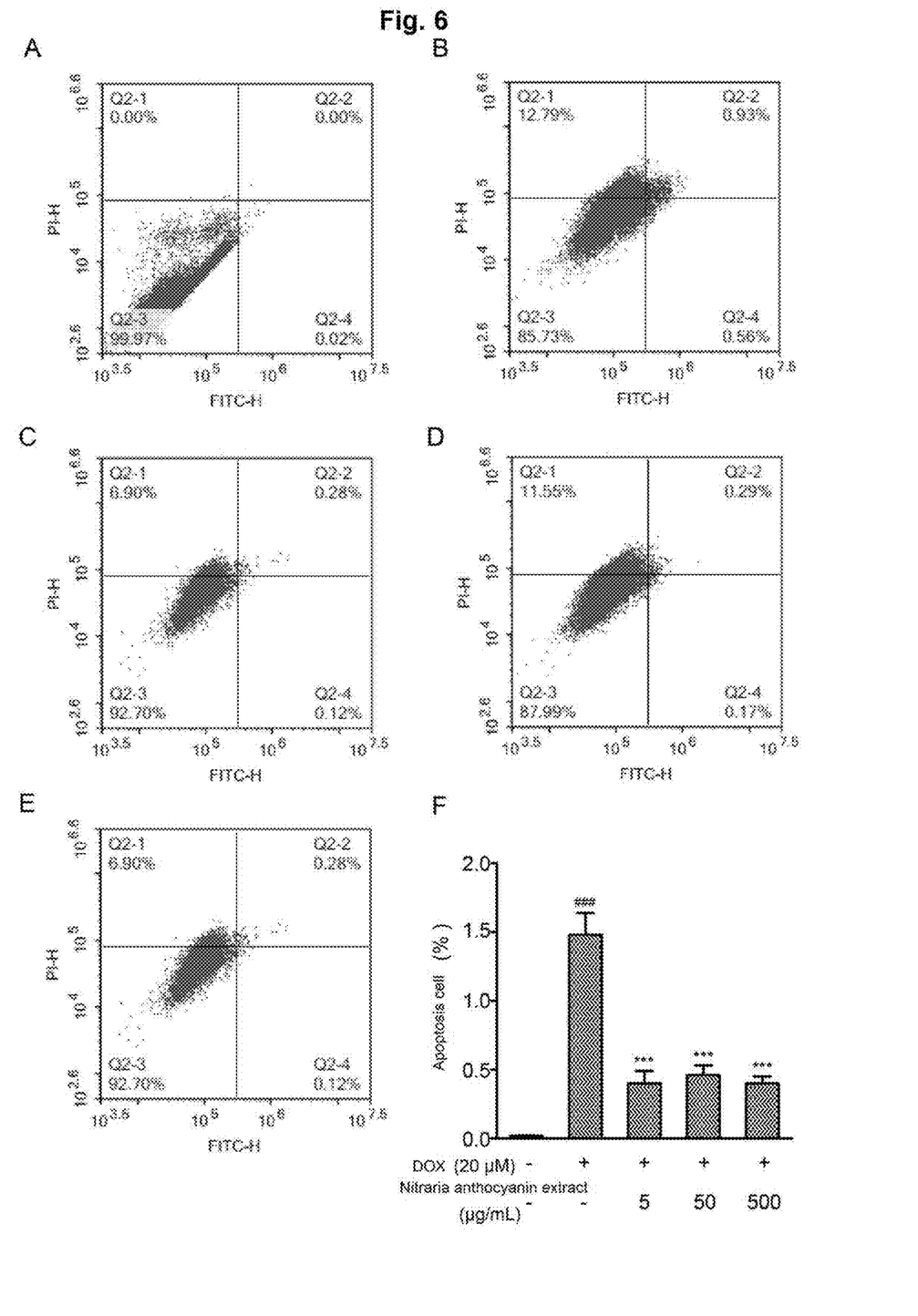
FIG. 6 shows a cell apoptosis degree of a cardiomyocyte H9c2 in embodiment 4, wherein A-E are a measured result map of a flow cytometry (A: a blank control group, B: a DOX treated cell damage model group, C: a 5 μg/mL *nitraria* anthocyanin extract treated group, D: a 50 μg/mL *nitraria* anthocyanin extract treated group, E: a 500 μg/mL *nitraria* anthocyanin extract treated group), and F is a summarized result map for data of all experimental groups.
Figure 7A:
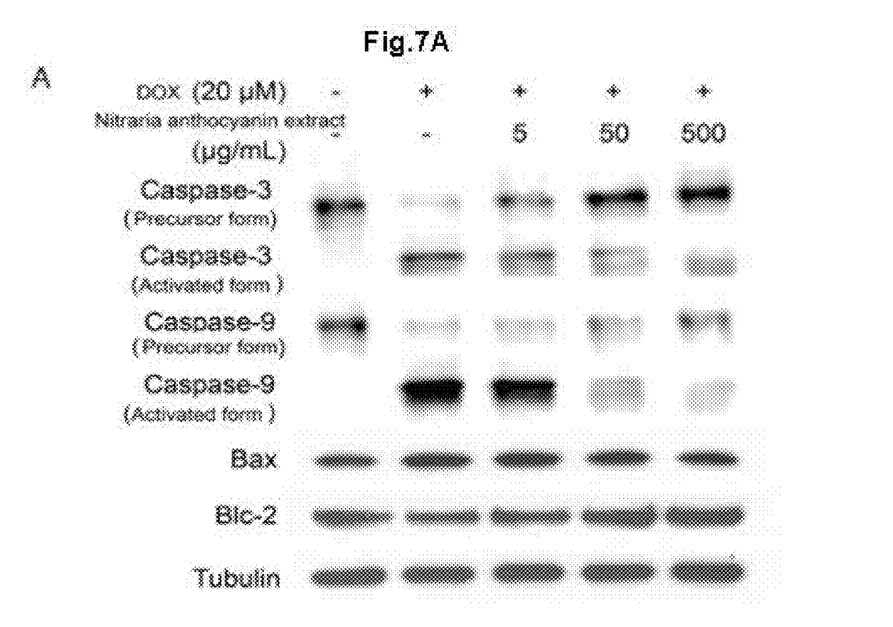
Figure 7B:
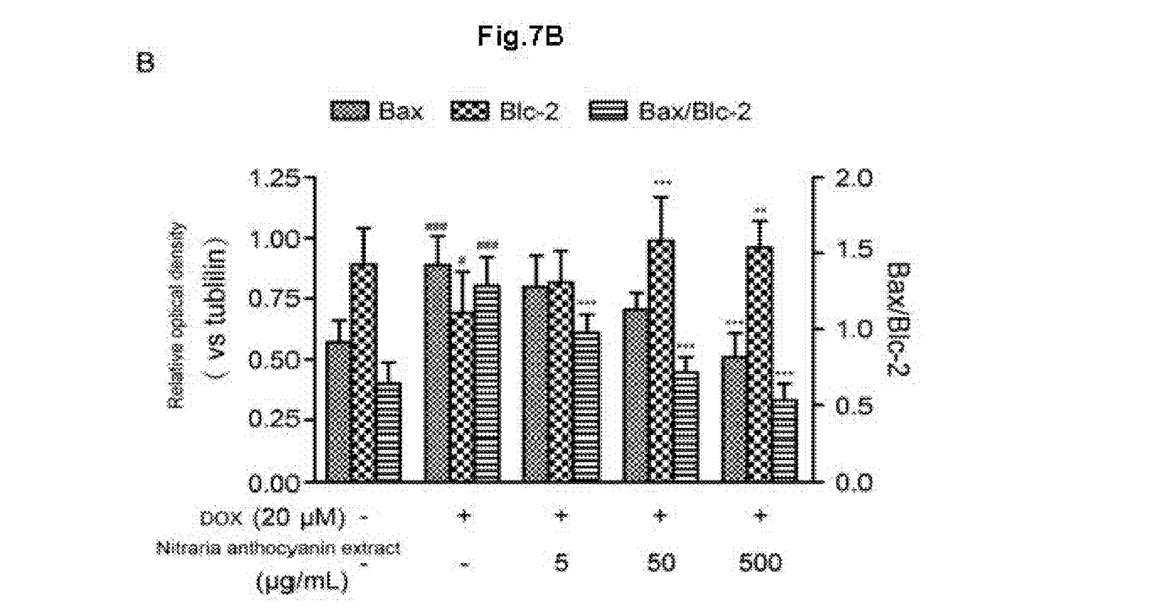
FIG. 7B is a Bax-α and Bcl-2 protein expression analysis result map.
Figure 7C:
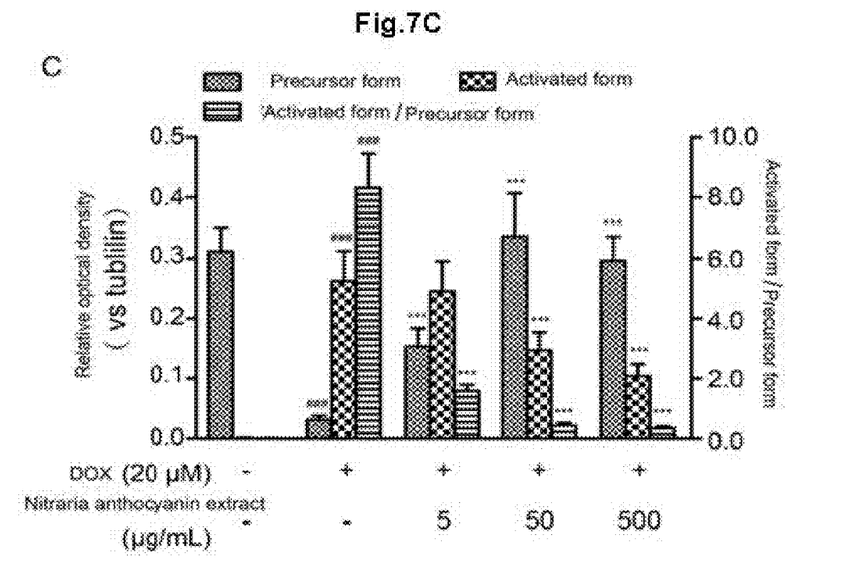
FIG. 7C is a Caspase-3 protein expression analysis result map.
Figure 7D:
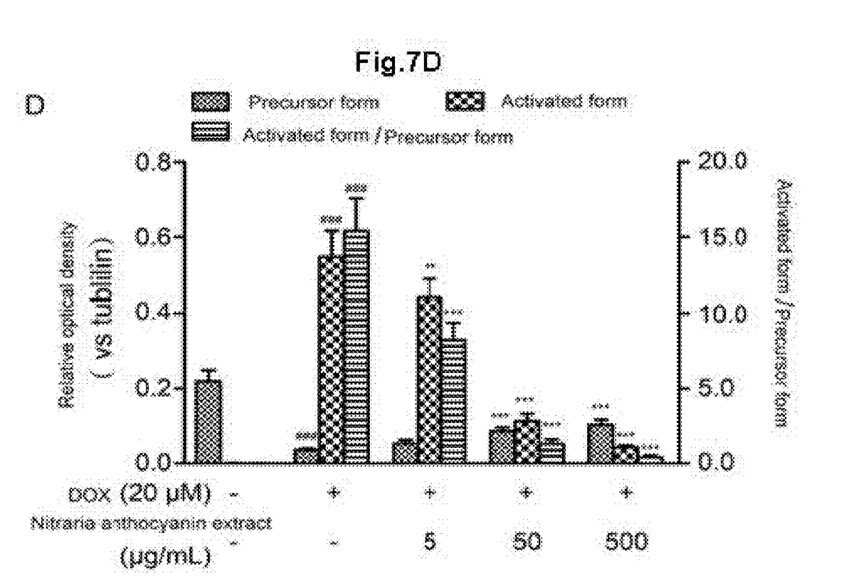
FIG. 7D is a Caspase-9 protein expression analysis result map, #$p<0.05$ and ###$p<0.001$ indicate that there is a significant difference as compared to a blank control group, and $p<0.01$ and *$p<0.001$ indicate that there is a significant difference as compared to a model group.

A rat cardiomyocyte cell line H9c2: a DMEM culture medium (containing 10% new-born calf serum, 2 mM glutamate and 1% streptomycin/penicillin) was employed to culture, and a culture condition was an aseptic environment at 37° C. and 5% C02. The culture medium was replaced once every 2-3 d, and when cells were cultured for 24 h and 80% were aggregated, a medicament treatment was performed. A control group, a model group (containing 20 μM DOX), and a *nitraria* anthocyanin extract experimental group (containing 20 μM DOX and 5-500 μg/mL *nitraria* anthocyanin extract) were respectively provided, and after they were treated for 24 h, a change in cardiomyocyte apoptosis was detected by a flow cytometer according to operating instructions of a kit by employing an FITC-Annexin V/propidium iodide (PI) fluorescence double staining method. According to experimental results as shown in FIG. 6, after the 20 μM DOX is treated for 24 h, a number of FITC-Annexin V positive cells is increased from 0.02% to 1.49%; and after the DOX and the 5-500 μg/mL *nitraria* anthocyanin extract are co-treated for 24 h, the number of the FITC-Annexin V positive cells is only increased to 0.40-0.46%. It is indicated that the *nitraria* anthocyanin extract has obvious protection effect to cardiomyocyte apoptosis caused by the DOX.

Embodiment 5

A rat cardiomyocyte cell line H9c2: a DMEM culture medium (containing 10% new-born calf serum, 2 mM glutamate and 1% streptomycin/penicillin) was employed to culture, and a culture condition was an aseptic environment at 37° C. and 5% $CO_2$. The culture medium was replaced once every 2-3 d, and when cells were cultured for 24 h and 80% were aggregated, a medicament treatment was performed. A control group, a model group (containing 20 μM DOX), and a *nitraria* anthocyanin extract experimental group (containing 20 μM DOX and 5-500 μg/mL *nitraria* anthocyanin extract) were respectively provided, and after they were treated for 24 h, the cells were scrapped, and were collected by centrifugation; and after being cleaned by a phosphate buffer, the cells were resuspended in a lysis buffer. After cell debrises were removed by the centrifugation, a supernatant was collected and a soluble protein concentration was determined using a BCA protein concentration assay kit. A protein solute, after being separated by 12% SDS-PAGE electrophoresis, was transferred to a PVDF membrane and thereafter was labeled by bcl-2, bax, caspase-3 and caspase-9 antibodies. An optical density of a band was determined by Quantity One software (v4.62, American Bio-Rad Company). And αβ-tubulin was taken as a protein sample loading internal reference substance. According to experimental results (as shown in FIG. 7A-7D), after the 20 μM DOX is treated for 24 h, a bax protein expression is significantly increased, a bcl-2 protein expression is significantly reduced, and a Bax/Bcl-2 protein expression ratio is increased to two times of a normal cell. At the meantime, the protein expressions for caspase-3 and caspase-9 after being cut and activated are significantly increased; after the DOX and the 5-500 μg/mL *nitraria* anthocyanin extract are co-treated for 24 h, the increase of the bax protein expression and the reduction of the bcl-2 protein expression are significantly inhibited. Compared with the model group, an increment in the Bax/Bcl-2 protein expression ratio is reduced by 1.32-2.42 times, and simultaneously, the increase of the cut and activated caspase-3 and caspase-9 protein expression due to the DOX is also significantly inhibited (P<0.001). It is indicated that the *nitraria* anthocyanin extract can inhibit the cascaded activation of Caspase protein families by adjusting the expression of an apoptosis induced gene (bax) and an apoptosis inhibited gene (bcl-2), thereby protecting the cardiomyocyte and relieving the cell apoptosis damage caused by the DOX.

Embodiment 6

Figure 8:
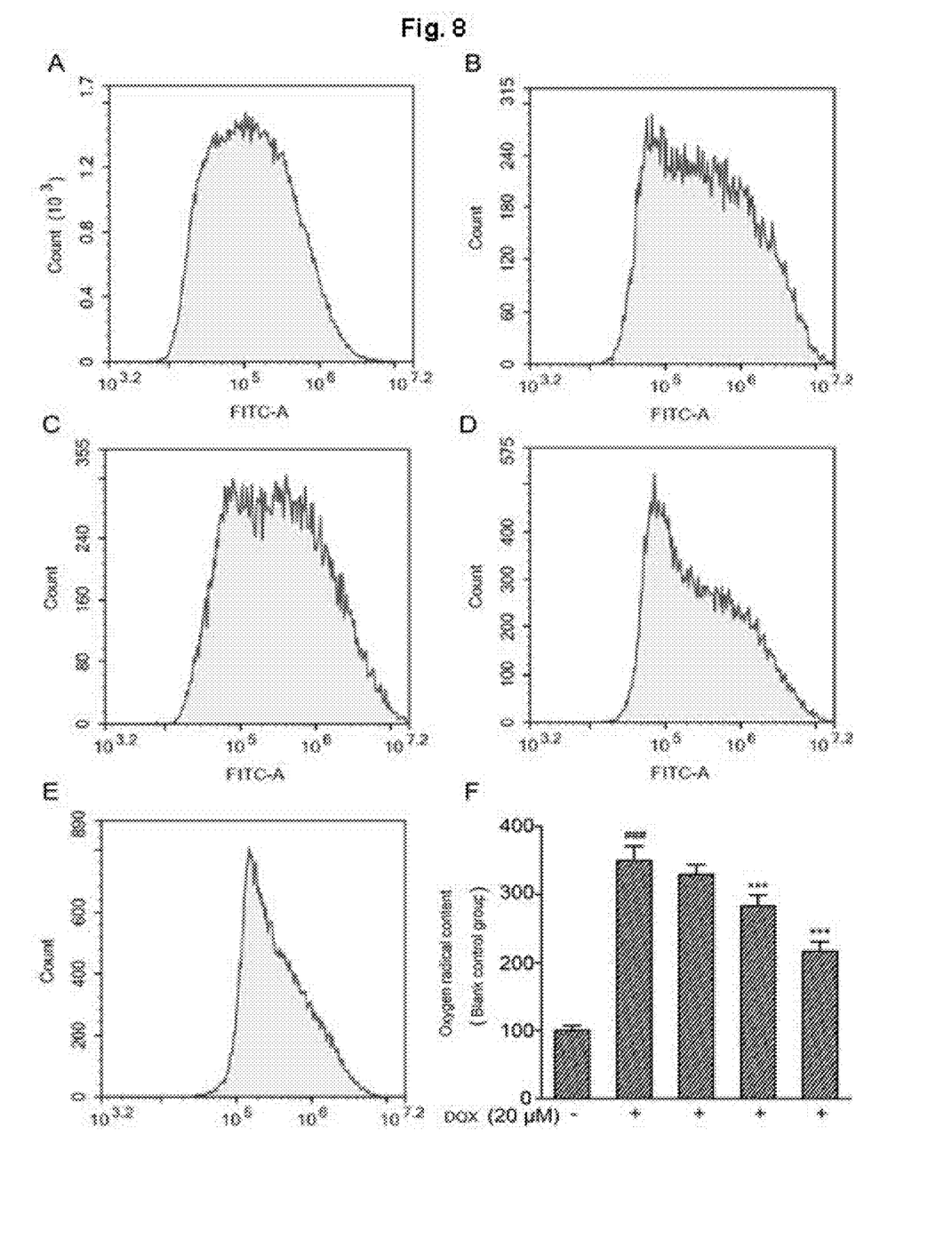
FIG. 8 shows an aggregation degree of reactive oxide species (ROS) of a cardiomyocyte H9c2 in embodiment 6, wherein A-E are a measured result map of a flow cytometry (A: a blank control group, B: a DOX treated cell damage model group, C: a 5 μg/mL *nitraria* anthocyanin extract treated group, D: a 50 μg/mL *nitraria* anthocyanin extract treated group, E: a 500 μg/mL *nitraria* anthocyanin extract treated group), and F is a summarized result map for data of all test groups.

A rat cardiomyocyte cell line H9c2: a DMEM culture medium (containing 10% new-born calf serum, 2 mM glutamate and 1% streptomycin/penicillin) was employed to culture, and a culture condition was an aseptic environment at 37° C. and 5% $CO_2$. The culture medium was replaced once every 2-3 d, and when cells were cultured for 24 h and 80% were aggregated, a medicament treatment was performed. A control group, a model group (containing 20 μM DOX), and a *nitraria* anthocyanin extract experimental group (containing 20 μM DOX and 5-500 μg/mL *nitraria* anthocyanin extract) were respectively provided, and after they were treated for 24 h, 2', 7'-dichlorodihydro-fluorescein diacetate (DCFH-DA, 20 μM) was added to incubate for 20 min at 37° C., and a flow cytometer was employed to detect an aggregated level of cardiomyocyte ROS. According to experimental results (as shown in FIG. 8), after the 20 μM DOX is treated for 24 h, the aggregated level of the cardiomyocyte ROS is increased to 3.5 times of a normal cell; and after the DOX and the 5-500 μg/mL *nitraria* anthocyanin extract are co-treated for 24 h, the aggregated level of the cardiomyocyte ROS only is 2.16-3.29 times of the normal cell. It is indicated that the *nitraria* anthocyanin extract can protect cardiomyocyte damage caused by the DOX by reducing an ROS level in the cell.

Embodiment 7

Figure 9:
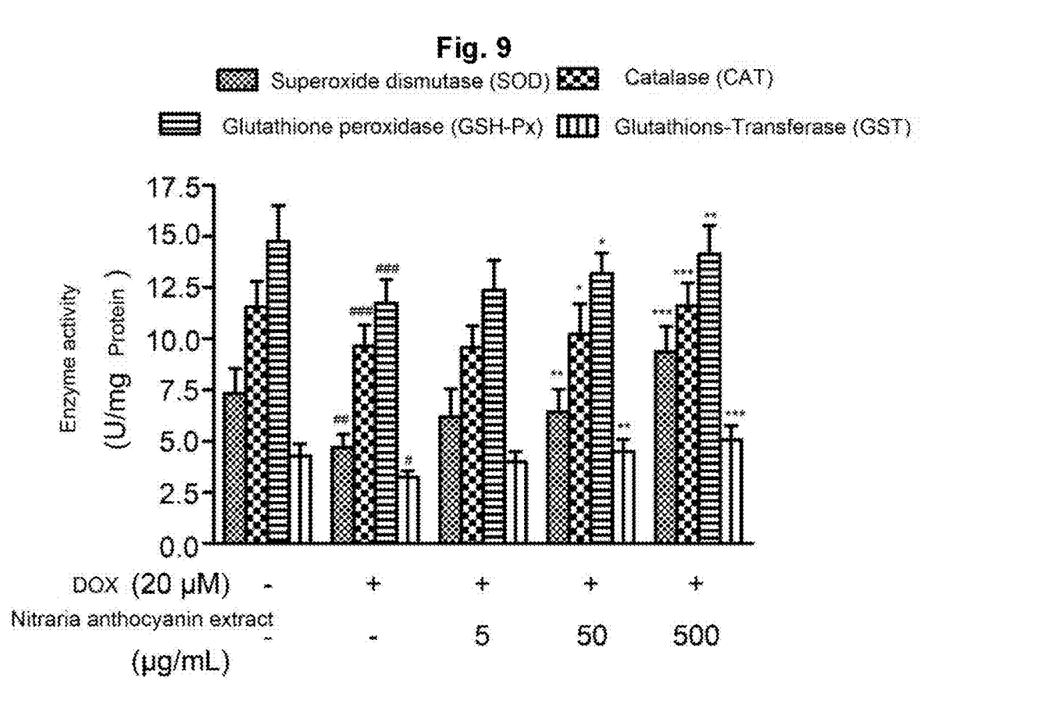
FIG. 9 shows a key antioxidase level and glutathione redox cycling of a cardiomyocyte H9c2 in embodiment 7.
Figure 10:
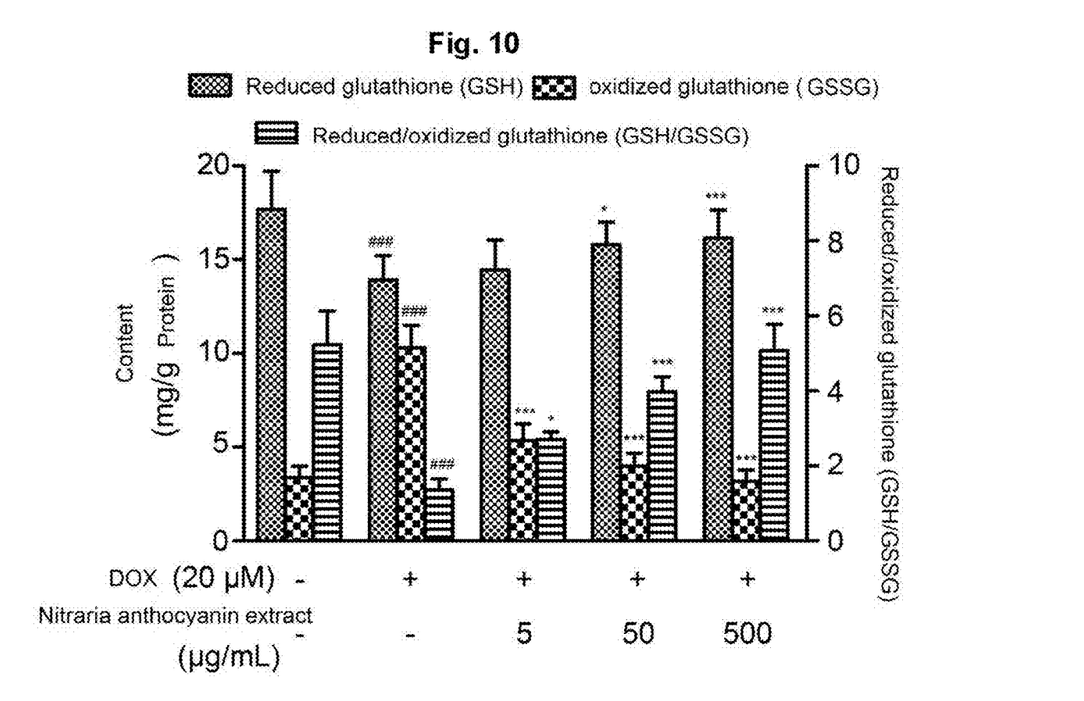
FIG. 10 shows a glutathione redox cycling of the cardiomyocyte H9c2 in embodiment 7.

A rat cardiomyocyte cell line H9c2: a DMEM culture medium (containing 10% new-born calf serum, 2 mM glutamate and 1% streptomycin/penicillin) was employed to culture, and a culture condition was an aseptic environment at 37° C. and 5% $CO_2$. The culture medium was replaced once every 2-3 d, and when cells were cultured for 24 h and 80% were aggregated, a medicament treatment was performed. A control group, a model group (containing 20 μM DOX), and a *nitraria* anthocyanin extract experimental group (containing 20 μM DOX and 5-500 μg/mL *nitraria* anthocyanin extract) were respectively provided, and after they were treated for 24 h, the cells were collected by centrifugation and then resuspended in a cell lysis buffer. A supernatant was collected by the centrifugation, and according to operation instructions of a kit, levels of a superoxide dismutase (SOD), a catalase (CAT), a glutathione peroxidase (GSH-Px) and a glutathions-transferase (GST) as well as contents of a reduced glutathione (GSH) and an oxidized glutathione (GSSG) were detected. According to experimental results (as shown in FIG. 9 and FIG. 10), after the 20 μM DOX is treated for 24 h, the levels of key antioxidases in the cardiomyocyte are significantly reduced, the GSH content is significantly reduced and the GSSG content is significantly increased. Compared with a normal cell, the levels of the SOD, the CAT, the GSH-Px and the GST of the cardiomyocyte in the model group are respectively reduced by 35.93%, 16.62%, 20.42% and 23.79% and a GSH/GSSG ratio is reduced by 74.10%. And after the DOX and the 5-500 μg/mL *nitraria* anthocyanin extract are co-treated for 24 h, the levels of the key antioxidases such as SOD and the GSH/GSSG ratio are significantly relieved to reduce, and under a 500 μg/mL dose, all are up to or close to the levels of the normal cell. It is indicated that the *nitraria* anthocyanin extract can significantly improve the endogenous antioxidant ability of the cardiomyocyte and promotes the redox cycling of glutathione in the cell; and in such a way, the cardiomyocyte damage caused by the DOX is protected.

Embodiment 8

A cell-free in vitro experimental method was employed to determinate a reducing power, a $Fe^{2+}$ chelating ability and an ability to scavenge a superoxide radical, a hydroxyl radical, a 1,1-diphenyl-2-picrylhydrazyl (DPPH) radical and a hydrogen peroxide ($H_2O_2$) of the *nitraria* anthocyanin extract. An ascorbic acid (ACS grade, content≥99%, Shanghai Aladdin Biochemical Technology Co., Ltd.) and a grape seed extract (GSE, polyphenol content: 99.04%, batch No.: 002-1401001-02, Tianjin Jianfeng Natural Product R&D Co., Ltd.) were taken as positive control drugs.

Figure 11:
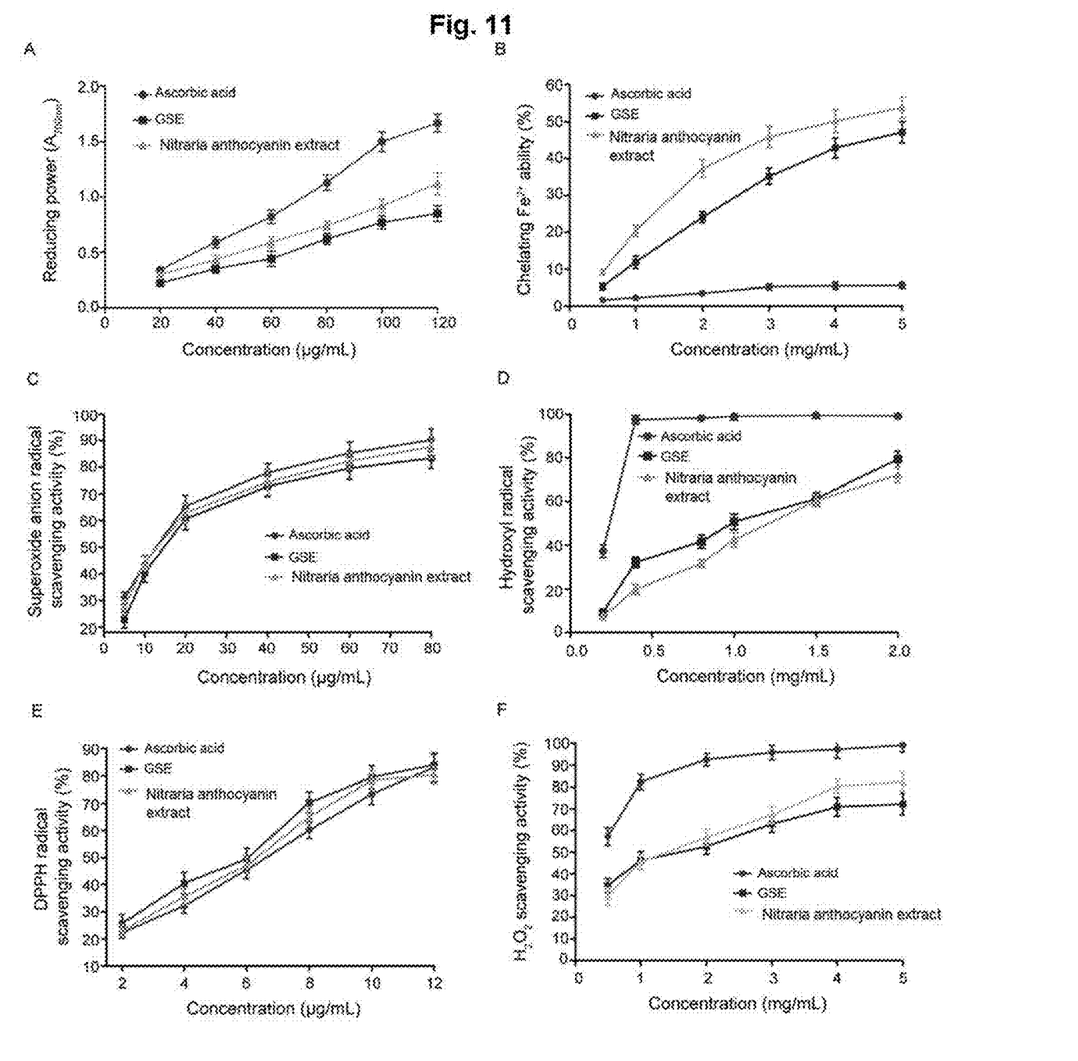
FIG. 11 shows a reducing power, a $Fe^{2+}$ chelating ability, and a key radical and its intermediate species scavenging ability of a cell-free in-vitro experimental method to a *nitraria* anthocyanin extract in embodiment 8, wherein A is the reducing power, B is the $Fe^{2+}$ chelating ability, C is a superoxide radical scavenging rate, D is a hydroxyl radical scavenging rate, E is a 1,1-diphenyl-2-picrylhydrazyl (DPPH) radical scavenging rate, and F is a $H_2O_2$ scavenging rate.

Experimental results show that the *nitraria* anthocyanin extract has significant reducing power, good $Fe^{2+}$ chelating ability and excellent ability to scavenge the superoxide radical, the hydroxyl radical, the DPPH radical and the $H_2O_2$. Particularly, the reducing power, the $Fe^{2+}$ chelating ability and the efficiency ($EC_{50}$) to scavenge the superoxide radical, the hydroxyl radical and the $H_2O_2$ all are superior to the positive control drug GSE (refer to FIG. 11). It is indicated that the *nitraria* anthocyanin extract can effectively prevent the DOX from obtaining an electron or $Fe^{2+}$ from converting into a semiquinone form or forming a DOX-$Fe^{2+}$ radical complex having a great harm to cardiomyocyte mitochondria, and effectively scavenges two main radicals (hydroxyl radical and superoxide radical) produced by DOX induced cardiomyocyte oxidative stress and a main medium ($H_2O_2$) which forms the radicals; and thus, the cardiomyocyte damage caused by the DOX is protected.

Embodiment 9

All mice were classified into four groups at random: a normal control group, a DOX model group, a grape seed extract positive control group and a *nitraria* anthocyanin extract treatment group, there were 12 mice in each group, and the cardiotoxicity of the mice was induced using single intraperitoneal injection of the DOX (15 mg/kg). Mice in the normal control group were treated by intraperitoneally injecting equal volumes of physiological saline. For the grape seed extract positive control group and the *nitraria* anthocyanin extract treatment group, after the DOX injection, intragastric administration was performed respectively and continuously for 5 d with a dosage being 10 mg/kg/d. The mice in the model group and the normal control group were given with the same volume of the physiological saline for the intragastric administration and all were put to death after 7 d, and serum samples and cardiac tissue lysates were respectively collected. According to operating instructions of an ELISA kit, levels of LDH and CK in serums of the mice in each group and contents of malondialdehyde and glutathione in cardiac tissues of the mice were respectively measured. According to results as shown in table 2 (Effect of *Nitraria* Anthocyanin Extract on LDH and CK Levels in Serums and Malondialdehyde and Glutathione Levels in Cardiac Tissues of DOX-Induced Cardiotoxicity Mice), the single intraperitoneal injection of the DOX (15 mg/kg) can significantly increase the levels of the LDH and the CK in the serums and the malondialdehyde in the cardiac tissues of the mice, and reduce the level of the glutathione in the cardiac tissues. The *nitraria* anthocyanin extract at 10 mg/kg/d may significantly lower the increase of the levels of the LDH and the CK in the serums and the malondialdehyde in the cardiac tissues of the mice due to the DOX, and significantly accelerates the reduction of the level of the glutathione in the cardiac tissues. And particularly, the activity of the *nitraria* anthocyanin extract is obviously superior to the positive control drug (grape seed extract) and shows good prevention and treatment effect for the cardiac toxicity induced by Anthracydines.

*Bulgaria inquinans* (Fries). Food Chem. 2013, 138, 1470-1475.: ④Halliwell, B., Gutteridge, J. M. C. and Aruoma, O. I., The deoxyribose method: A simple 'test-tube' assay for determination of rate constants for reactions of hydroxyl radicals. Anal. Biochem. 1987, 165, 215-219; ⑤Kansci, G., Dongo, E. and Genot, C., 2,2-Diphenyl-1-picrylhydrazyl (DPPH*) test demonstrates antiradical activity of *Dorstenia psilurus* and *Dorstenia ciliata* plant extracts. Mol. Nutr. Food Res. 2003, 47, 434-437; ⑥Pick, E., and Mizel, D., Rapid microassays for the measurement of superoxide and hydrogen peroxide production by macrophages in culture using an automatic enzyme immunoassay reader. J. Immunol. Methods 1981, 46(2), 211-226.

Embodiment 10

The anthocyanin extract mentioned in embodiments 9 to 12 refers to an extract prepared by the following steps: adding 70% ethanol to pomaces, which are produced by *nitraria* fruits or after the *nitraria* fruits are squeezed into juice, according to a solid-liquid ratio of 1:15-1:30 g/mL and extracting for 30-90 min at 55-65° C.; concentrating an extracting solution under a reduced pressure till there is no ethanol, separating by a weakly polar macroporous adsorption resin, rinsing with three times of water by a column volume, then rinsing with the 70% ethanol, collecting an effluent, concentrating and drying to obtain the anthocyanin extract; and the anthocyanin extract is an extract having a total anthocyanin content greater than 700 mg CGE/g and a total antioxidant capacity greater than 200 mg TE/g.

TABLE 2

| | | Serum | | Cardiac Tissue | |
| | | | | Malondialdehyde | Glutathione |
| Serial No. | Experimental Group | LDH U/mL | CK U/mL | nmol/mg protein | nmol/mg protein |
| --- | --- | --- | --- | --- | --- |
| 1 | Normal control group | 4.03 ± 0.22 | 1.66 ± 0.34 | 1.25 ± 0.27 | 27.62 ± 3.57 |
| 2 | DOX-induced cardiotoxicity model group | 7.52 ± 0.27*** | 3.26 ± 0.35** | 4.30 ± 0.33** | 15.58 ± 4.02** |
| 3 | Grape seed extract positive control group (10 mg/kg/d) | 5.73 ± 0.25## | 2.05 ± 0.25## | 2.73 ± 0.28## | 19.91 ± 2.94# |
| 4 | Nitraria anthocyanin extract treatment group (10 mg/kg/d) | 4.95 ± 0.24## | 1.89 ± 0.24## | 2.32 ± 0.29## | 22.30 ± 3.71## |

Specific operations of experiments in the embodiments 1 to 9 are respectively described as the following literatures: ①Müller, L., Theile, K. and Böhm, V., In vitro antioxidant activity of tocopherols and tocotrienols and comparison of vitamin E concentration and lipophilic antioxidant capacity in human plasma. Mol. Nutr. Food Res. 2010, 54, 731-742; ②Dinis, T. C. P., Madeira, V. M. C. and Almeida, L. M., Action of phenolic derivatives (acetaminophen, salicylate, and 5-aminosalicylate) as inhibitors of membrane lipid peroxidation and as peroxyl radical scavengers. Arch. Biochem. Biophys. 1994, 315, 161-169; ③i, H., Gao, T., Li, Z, Ji, L. et al., Structural elucidation and antioxidant activity of a water-soluble polysaccharide from the fruit bodies of The anthocyanin extract having an addition amount of 30% and excipients (glycerol, soybean oil, maize oil, and beewax, etc.) having a total addition amount of 70% were prepared into a soft capsule which could prevent and treat the cardiac toxicity induced by Anthracyclines. A specific preparation method of the preparation was as follows: sieving the *nitraria* anthocyanin extract by 100-200 meshes, then mixing with the soybean oil and the beeswax, grinding uniformly via a colloid mill such that drugs are uniformly suspended in the excipients in a manner of fine particles, and preparing into the soft capsule by employing a dropping method or a pressing method.

Embodiment 11

The anthocyanin extract having an addition amount of 10% and auxiliary materials (sucrose, lactase, microcrystalline cellulose, modified starch, silicon dioxide, and magnesium stearate, etc.) having a total addition amount of 90% were prepared into a hard capsule which could prevent and treat the cardiac toxicity induced by Anthracyclines. A specific preparation method of the preparation was as follows: sieving the *nitraria* anthocyanin extract by 200-300 meshes, then mixing with the microcrystalline cellulose, the modified starch and the silicon dioxide, uniformly mixing via a powder mixer and encapsulating into the hard capsule.

Embodiment 12

The anthocyanin extract having an addition amount of 20% and auxiliary materials (xylitol, honey, citric acid and salt, etc.) having a total addition amount of 80% were prepared into an oral liquid which could prevent and treat the cardiac toxicity induced by Anthracyclines. A specific preparation method of the preparation was as follows: dissolving the *nitraria* anthocyanin extract in an appropriate amount of an ethanol solution, adding to a preparation tank together with a solution containing an appropriate amount of the auxiliary materials such as the xylitol, the honey, the citric acid, the salt and the like after residues are removed by centrifugation, stirring to mix uniformly and aseptically encapsulating mixed liquor after being sterilized and homogenized into the oral liquid.

Embodiment 13

The anthocyanin extract having an addition amount of 40% and matrixes (polyethylene glycol and the like) having a total addition amount of 60% were prepared into an oral dropping pill which could prevent and treat the cardiac toxicity induced by Anthracyclines. A specific preparation method of the preparation was as follows: mixing the *nitraria* anthocyanin extract with polyethylene glycol 6000, dripping into a dimethylsilane condensate after heating and stirring to disperse fully, collecting a dropping pill, removing dimethylsilane on a surface of the dropping pill and preparing into the oral dropping pill.

The above description is only preferred embodiments of the present disclosure and is not intended to limit the present disclosure. For persons skilled in the art, the present disclosure may have various modifications and changes. Any modification, equivalent replacement, or improvement made within the spirit and principle of the present disclosure shall all fall within the protection scope of the present disclosure.

What is claimed is:

1. A method for preventing and treating cardiac toxicity induced by Anthracyclines, said method comprising administering a pharmaceutical composition comprising an effective dose of an anthocyanin extract to a subject in need thereof, and the anthocyanin extract is obtained from mature fruits of a zygophyllaceous *nitraria* plant and having a total anthocyanin content greater than 700 mg CGE/g and a total antioxidant capacity greater than 200 mg TE/g; wherein an anthocyanidin as a source of the anthocyanin extract comprises cyanidin, delphinidin, malvidin, pelargonidin, peonidin and petunidin.

2. The method according to claim 1, wherein the anthocyanin extract comprises six or more selected from groups composed of cyanidin-3-O-diglucoside, cyanidin-3-O-sambubioside, cyanidin-3-O-(cis-6"-O-coumaroyl)-diglucoside, cyanidin-3-O-(trans-6"-O-coumaroyl)-diglucoside, cyanidin-3-O-(6"-O-coumaroyl)-glucoside, delphinidin-3-O-(6"-O-coumaroyl)-glucoside, 5-O-glucoside, delphinidin-3-O-(6"-O-coumaroyl)-glucoside, malvidin-3-O-glucoside, malvidin-3-O-(6"-O-acetyl)-glucoside, malvidin-3-O-(6"-O-coumaroyl)-glucoside, 5-O-glucoside, malvidin-3-O-(cis-6"-O-coumaroyl)-glucoside, malvidin-3-O-(trans-6"-O-coumaroyl)-glucoside, pelargonidin-3-O-(6"-O-coumaroyl)-diglucoside, peonidin-3-O-(6"-O-coumaroyl)-glucoside, peonidin-3-O-(6"-O-coumaroyl)-glucoside, 5-O-glucoside and petunidin-3-O-(6"-O-coumaroyl)-glucoside; and the anthocyanidin as the source of the anthocyanin extract comprises the cyanidin, the delphinidin, the malvidin, the pelargonidin, the peonidin and the petunidin.

3. The method according to claim 1, wherein the anthocyanin extract is prepared by the following method: adding 60-90% ethanol to pomaces, which are produced by *nitraria* fruits or after the *nitraria* fruits are squeezed into juice, according to a solid-liquid ratio of 1:15-1:30 g/mL, and extracting for 30-90 min at 55-65° C.; concentrating an extracting solution under a reduced pressure till there is no ethanol, separating by a weakly polar macroporous adsorption resin, rinsing with three times of water by a column volume, then rinsing with the 60-90% ethanol, collecting an effluent, concentrating and drying to obtain the anthocyanin extract.

4. The method according to claim 1, wherein the anthracyclines are one or more of doxorubicin (DOX), daunorubicin (DNR), aclacinomycin, epirubicin, pirarubicin, idarubicin, valrubicin or mitoxantrone.

5. The method according to claim 1, wherein a dosage form of the pharmaceutical composition is any one of a capsule, a tablet, an oral liquid, a granule and a dropping pill.

* * * * *